United States Patent [19]
Ferguson

[11] Patent Number: 6,060,460
[45] Date of Patent: May 9, 2000

[54] USE OF BETAGLYCAN TO REDUCE SCARRING

[75] Inventor: Mark William James Ferguson, Furness Vale, United Kingdom

[73] Assignee: The Victoria University of Manchester, Manchester, United Kingdom

[21] Appl. No.: 09/011,061

[22] PCT Filed: Jul. 31, 1996

[86] PCT No.: PCT/GB96/01841

§ 371 Date: May 14, 1998

§ 102(e) Date: May 14, 1998

[87] PCT Pub. No.: WO97/05892

PCT Pub. Date: Feb. 20, 1997

[30] Foreign Application Priority Data

Aug. 4, 1995 [GB] United Kingdom ............... 9516073

[51] Int. Cl.[7] ............... A61K 31/715; A61K 38/16; A61K 31/725; C07K 9/00
[52] U.S. Cl. ............... 514/54; 514/8; 514/56; 536/118; 536/123.1; 530/350; 530/395
[58] Field of Search ............... 514/54, 56, 8; 536/118, 123.1; 530/350, 395

[56] References Cited

U.S. PATENT DOCUMENTS 5,453,492  9/1995  Bützow et al. ............... 530/350

FOREIGN PATENT DOCUMENTS

| | | |
|---|---|---|
| WO-A-9217206 | 10/1992 | WIPO . |
| 93/10215 | 5/1993 | WIPO . |
| WO-A-9319769 | 10/1993 | WIPO . |
| WO-A-940815 | 5/1994 | WIPO . |
| WO-A-9510610 | 4/1995 | WIPO . |

OTHER PUBLICATIONS

The Journal of Cell Biology, vol. 124, No. 4, Feb. 1994, pp. 557–568, Lopez–Casillas et al, "Betaglycan Can Act as a Dual Modulator of TFG–Beta Access to Signaling Receptors: Mapping of Ligand Binding and GAG Attachment Sites".

Journal of Cell Science, vol. 108, Mar. 1995, pp. 985–1002, Shah et al, Neutralisation of TGF–Beta1 and TGF–Beta2 or Exogenous Addition of TGF–Beta3 to Cutaneous Rat Wounds Reduces Scarring.

Journal of Cell Science, vol. 107, 1994, pp. 1137–1157, Shah et al, "Neutralising Antibody to TGF–Beta1,2 Reduces Cutaneous Scarring in Adult Rodents".

Border, Wayne A., M.D. et al., "Transforming Growth Factor β in Tissue Fibrosis", The New England Journal of Medicine, vol. 331, No. 19, Nov. 10, 1994, pp. 1286–1292.

*Primary Examiner*—Gary L. Kunz
*Assistant Examiner*—Everett White
*Attorney, Agent, or Firm*—Nixon & Vanderhye P.C.

[57] ABSTRACT

The present invention concerns soluble betaglycan for use in promoting the healing of wounds or fibrotic disorders with reduced scarring, together with methods for same.

9 Claims, No Drawings

USE OF BETAGLYCAN TO REDUCE SCARRING

This application is a 371 of PCT/GB96/01841, filed Jul. 31, 1996.

The present invention concerns pharmaceutical compositions for promoting the healing of wounds or fibrotic disorders, in particular for promoting the healing of wounds or fibrotic disorders with reduced scarring.

By "wounds or fibrotic disorders" is meant any condition which may result in the formation of scar tissue. In particular, this includes the healing of skin wounds, the repair of tendon damage, the healing of crush injuries, the healing of eye wounds, including wounds to the cornea, the healing of central nervous system (CNS) injuries, conditions which result in the formation of scar tissue in the CNS, scar tissue formation resulting from strokes, and tissue adhesion, for example, as a result of injury or surgery (this may apply to e.g. tendon healing and abdominal strictures and adhesions). Examples of fibrotic disorders include pulmonary fibrosis, glomerulonephritis, cirrhosis of the liver, and proliferative vitreoretinopathy.

By "reduced scarring" is meant reduced level of scarring relative to an untreated wound or fibrotic disorder.

In particular, there is a lack of compositions for promoting the healing of wounds or fibrotic disorders with reduced scarring. Scar tissue formation, although providing mechanical strength to a healed wound, can be unsightly and may impair the function of the tissue.

This is particularly the case in wounds which result in scar tissue formation in the CNS, the scar tissue inhibiting the reconnection of severed or re-growing nerve ends, so significantly affecting their function.

There is also a lack of compositions for treating and promoting the healing of chronic wounds, for example venous ulcers, diabetic ulcers and bed sores (decubitus ulcers), especially in the elderly and wheel chair bound patients. Such compositions may be extremely useful in patients where wound healing is either slow or in whom the wound healing process has not yet started. Such compositions may be used to "kick-start" wound healing and may then be used in combination with compositions for promoting healing with reduced scarring. Hence not only may a chronic wound be healed, but it may be healed with reduced scarring.

Betaglycan (BG), otherwise known as TGFβ (Transforming Growth Factor-β) receptor III (RIII), is a widely distributed membrane proteoglycan comprising a 100 kDa core protein with heparan- and chondroitin-sulphate side chains attached to it (see Lopez-Casillas et al., 1991, Cell, 67: 785–795). TGF-β binds to the BG core protein, not requiring the glycosaminoglycan (GAG) side chains for this interaction, whilst FGF-2 binds to BG through the heparan-sulphate side-chains (Cheifetz, S. et al., 1988, J. Biol. Chem., 263: 16984–16991).

The BG core protein comprises:

i) An extracellular domain;

ii) a transmembrane domain; and iii) an intracellular domain having no recognisable signalling structure.

Cells are able to release the extracellular domain via a cleavage site near the transmembrane domain, and this appears to occur in vivo, soluble BG (solBG) being found in the serum (Andres, J. L. et al., 1989, J. Biol. Chem., 109: 3137–3145).

TGF-β binds to various membrane proteins (see Massague, J. et al., 1994, Trends in Cell Biol., 4: 172–178 for a review), two of which, TGF-β receptors I and II (RI and RII) form a signalling receptor complex. RI appears to require the presence of RII to bind ligand and RII appears to require the presence of RI for signalling, but not for ligand binding (see Wrana, J. L. et al., 1992, Cell, 71: 1003–1014). TGFβ receptor isoforn specificity may be conferred by the three different receptor types since RI and RII bind TGFβ$_1$ and TGFβ$_3$ with much greater affinity than TGFβ$_2$, this difference being most pronounced in cells which lack BG. Expression of BG correlates with elevated binding of all TGFβs to RII and this correlation is particularly evident in the case of TGFβ$_2$, an isoforrn which has a low affinity for RI and RII in the absence of BG (see Lopez-Casillas, F. et al., 1993, Cell, 73: 1435–1444). An important function of membrane-anchored BG is the presentation of TGF-β to RII, forming a ternary complex, thus increasing receptor binding affinity and cell responsiveness to TGFβ.

Conversely, the soluble form of BG has a very different role to that of the membrane-anchored BG. Soluble BG binds to TGF-β and prevents the TGF-β molecules from binding to the cell-surface receptors, hence acting as a TGF-β antagonist (see Lopez-Casillas, F. et al., 1994, J. Cell Biol., 124: 557–568).

Hence BG in its different forms may act as a dual modulator of TGF-β access to signalling receptors.

Previous work into the effects of fibrotic and non-fibrotic growth factors upon wound healing (Shah, M. et al., 1994, J. Cell Sci., 107: 1137–1157; Shah, M. et al., 1995, J. Cell Sci., 108: 985–1002; WO 92/17206 and references therein) have shown that, in order to promote effective healing with reduced scarring, both TGFβ$_1$, and TGFβ$_2$ must be inhibited to a similar extent, experiments having shown that simply inhibiting TGFβ$_2$ alone results in no significant improvement in scarring. The present inventor has now found that, surprisingly, addition of soluble BG to a site (by "site" is meant a site of wounding or of a fibrotic disorder), in particular to a wound site, effects healing with reduced scarring.

The efficacy of these results is particularly surprising since they were achieved by the use of soluble BG alone, which is primarily specific to TGFβ$_2$, rather than the use of BG in combination with a neutralising composition specific to TGFβ$_1$, such a use apparently being necessary according to the prior art. Experiments (below) also show that, surprisingly, at particular concentrations of solBG, the level of TGFβ$_3$ in wounds is increased. Lower concentrations of solBG appear to have no effect upon the level of TGFβ$_3$, whereas higher concentrations have a negative effect upon the level of TGFβ$_3$. This is particularly significant since, unlike TGFβ$_1$, and TGFβ$_2$, TGFβ$_3$ promotes the healing of wounds and fibrotic disorders with reduced scarring (WO 93/19769). and this may help explain the anti-scarring effect of solBG.

According to the present invention there is provided soluble betaglycan or a fragment or a partially modified form thereof for use in promoting the healing of wounds or fibrotic disorders with reduced scarring.

The soluble betaglycan may for example comprise recombinant soluble betaglycan.

By "fragment" or "partially modified form" is meant a molecule which is capable of binding to TGFβ$_2$, performing the role of solBG as described above. Partial modification may for example be by way of substitution, deletion or addition of amino acid residues. A substitution may for example be a conserved substitution. Hence a partially modified form of solBG may be an homologue of solBG. It may for example have at least 40% homology with solBG.

It may for example have at least 50, 60, 70, 80, 90 or 95% homology with solBG.

The solBG may, for example, comprise at least the TGF-β binding fragment of solBG.

The solBG may promote the accelerated healing of wounds or fibrotic disorders. By "accelerated healing" is meant faster wound healing than that achieved by an untreated control wound.

The solBG may be at a concentration of between about 0.01 and 1 $\mu$M, for example about 0.1 $\mu$M. Experiments (below) have shown that the efficacy of solBG in promoting the healing of wounds is dose-dependent. Experiments (below) relate to rats only and optimal concentrations of solBG for promoting the healing of wounds or fibrotic disorders with reduced scarring in rats and other animals may be readily determined by experimentation.

The solBG may have a greater binding affinity for TGF$\beta_2$ than for TGF$\beta_1$, and TGF$\beta_3$. It may bind TGF$\beta_1$, TGF$\beta_2$ and TGF$\beta_3$ in a ratio of approximately 2:7:2 respectively.

The solBG may reduce the quantity of TGF$\beta_2$ which binds to cell-surface receptors.

The solBG may reduce the activation by TGP$\beta_2$ of cell-surface receptors.

The solBG may be used in conjunction with a pharmaceutically acceptable carrier, diluent or excipient.

The solBG may be used in conjunction with a composition for promoting the healing of wounds or fibrotic disorders with reduced scarring.

The solBG may be used in conjunction with a composition for promoting the healing of chronic wounds.

Also provided according to the present invention is a method of promoting the healing of wounds or fibrotic disorders with reduced scarring comprising the use of solBG or a fragment or a partially modified form thereof according to the present invention.

The solBG may be administered to a site of wounding or fibrosis.

The solBG may be administered in aliquots of about 100 $\mu$l.

The solBG may be administered either immediately before or immediately after wounding or onset. By "onset" is meant the onset of a fibrotic disorder. The solBG may be administered within about 120 hours of wounding/onset, for example about 48 or 24 hours after wounding/onset.

The solBG may be administered at least twice. It may, for example, be administered three times. It may, for example, be administered immediately prior to wounding or onset, approximately 24 hours after wounding or onset and approximately 48 hours after wounding or onset.

The invention will be further apparent from the following description which shows, by way of example only, one form of solBG for promoting the healing of wounds or fibrotic disorders with reduced scarring, and methods for same.

EXPERIMENTAL

Animals were tested for the effects of soluble BG (solBG) upon wound healing by wounding the animals and treating them with various concentrations of solBG and analysing the wounds (see 'Materials and Methods'). Results show that soluble BG, in particular at a concentration of between about 0.01 $\mu$M and 1 $\mu$M, more particularly at a concentration of about 0.1 $\mu$M, appears to have great potential as an anti-scarring agent. Wounds analysed at 7, 40 and 80 days post-wounding (pw) show both significantly improved scarring (i.e. less scarring) and increased (i.e. accelerated) wound healing over control wounds.

Materials and Method

Recombinant solBG (see Lopez-Casillas et al., 1991, Cell, 67: 785–795; Lopez-Casillas, F. et al., 1993, Cell, 11: 1435–1444; and Lopez-Casillas, F. et al., 1994, J. Cell Biol., 124: 557–568) supplied by F. Lopez-Casillas was dissolved in MEM (minimum essential medium) (serum free). 250 ng of solBG are equivalent to 50 $\mu$g of neutralising antibody (NAB) to TGF-β. Appropriate doses of solBG were calculated from the known effective concentrations of NAB to TGF-β(see Shah, M. et al., 1994, J. Cell Sci., 107: 1137-1157; Shah, M. et al., 1995, J. Cell Sci., 10: 985–1002; and Lopez-Casillas, F. et al., 1994, J. Cell Biol., 124: 557–568). Adult male Sprague-Dawley rats (200–250 g) were anaesthetised by halothane, nitrous oxide and oxygen inhalation. Four incisions, 1 cm in length and to the depth of and through the panniculus carnosus were made on the dorsal skin, equidistant from the midline and adjacent to the limbs. The wounds were left unsutured, to heal by secondary intention, in order to produce maximum scarring. One control wound on each animal was left untreated and one was infiltrated by injection with MEM alone, as a vehicle control. The two remaining wounds were injected with solBG at concentrations of 0.001 $\mu$M, 0.01 $\mu$M, 0.1 $\mu$M, 1 $\mu$M and 2 $\mu$M just prior to wounding, and on days 1 and 2 post-wounding. SolBG was applied to the wounds by intradermal injection in 100 $\mu$l MEM along the length of each wound margin. Four animals per dose of solBG per time point were used for each of 0.001 $\mu$M and 2 $\mu$M, and two animals per dose per time point for each of 0.001 $\mu$M, 0.1 $\mu$M and 1 $\mu$M (n=48 in total). Animals were harvested on each of the time points of 3, 5, 7 and 80 days pw. Animals were killed by chloroform overdose and wounds were harvested by excision from the surrounding tissue. Each wound was bisected, half the wound was rapidly frozen in OCT for cryosection and immunocytochemistry and half was fixed in formaldehyde for wax embedding and histology.

Results

Histology

There were few histological differences between wounds treated with the lower doses of solBG (0.001–0.1 $\mu$M) and control or vehicle control wounds five days after wounding. However, the wounds treated with 1 and 2 $\mu$M solBG appeared to be much narrower than the controls, but with a higher inflammatory cell infiltrate and more new blood vessels at the base of the wound. Similar observations were noted in wounds harvested 7 days after wounding.

The extent of scarring was examined 80 days after wounding. Treatment with 0.001 $\mu$M or 0.01 $\mu$M solBG resulted in no consistent improvement in scarring compared to controls. The collagen fibres within the wound were thin, densely packed and highly orientated, generally parallel to the epidermnis, in a typical scar formation. However when a dose of 0.1 $\mu$M solBG was applied to the wounds, the subsequent scarring was significantly improved. Collagen fibres within the treatment wounds were much thicker, more widely spaced and orientated in a more random fashion than in the control scars, and were more similar to the "basket weave" orientation of collagen fibres seen in the normal dermis. A dose of 1 $\mu$M solBG resulted in no consistent improvement in scarring, although some of the treated wounds were improved, whereas a dose of 2 $\mu$M resulted in either no improvement or as worse a scar as found in control wounds.

Immunocytochemistry

Wounds harvested 3 days after wounding were examined. There were no consistent differences in wound fibronectin content 3 days after wounding between control wounds and those treated with the various concentrations of solBG. Staining for TGFβ$_1$ revealed similar amounts of this cytokine, most evident within monocytes/macrophages, in treated and control wounds, except when a concentration of 1 or 2 μM solBG was applied. In these wounds TGFβ$_1$ levels appeared to be increased when compared to controls. Interestingly, staining for TGFβ$_3$, again mainly located within monocytes/macrophages, revealed a different pattern. Application of 0.001 μM solBG had no obvious effect on TGFβ$_3$ levels, but doses of 0.01 μM and particularly 0.1 μM, the treatment which showed the best improvement in scarring, resulted in increased staining for TGFβ$_3$ within the wound. Conversely, doses of 1 μM and 2 μM solBG resulted in lower levels of TGFβ$_3$ within the wound when compared to controls. Initial studies on the levels of TGFβ receptors within the wound, indicate increased expression of the type I receptor at the wound edge and in the adjacent dermis in wounds treated with 1 and 2 μM solBG.

I claim:

1. A method of promoting the healing of a wound with reduced scarring comprising administering at a wound site of a subject in need of such promotion an amount of soluble betaglycan or therapeutically effective fragment thereof sufficient to effect said promotion.

2. The method according to claim 1 wherein the soluble betaglycan or therapeutically effective fragment thereof is a recombinant molecule.

3. The method according to claim 1 wherein a composition comprising a concentration of between about 0.01 and 1 μM soluble betaglycan or therapeutically effective fragment thereof is administered to said wound.

4. The method according to claim 3 wherein said composition comprises a concentration of about 0.1 μM soluble betaglycan or therapeutically effective fragment thereof.

5. The method according to claim 3 wherein said composition comprises soluble betaglycan.

6. The method according to claim 1 wherein the soluble betaglycan or therapeutically effective fragment thereof binds TGFβ$_1$, TGFβ$_2$ and TGFβ$_3$ in a ratio of approximately 2:7:2 respectively.

7. The method according to claim 1 wherein the soluble betaglycan or therapeutically effective fragment thereof is administered either immediately prior to or immediately after wounding.

8. The method according to claim 1 wherein the soluble betaglycan or therapeutically effective fragment thereof is administered within about 120 hours of wounding.

9. The method according to claim 1 wherein the soluble betaglycan is administered.

* * * * *